(12) United States Patent
Laakkonen

(10) Patent No.: US 10,926,138 B2
(45) Date of Patent: Feb. 23, 2021

(54) EXERCISE DEVICE

(71) Applicant: TE3 OY, Espoo (FI)

(72) Inventor: Ari Laakkonen, Helsinki (FI)

(73) Assignee: TE3 OY, Helsinki (FI)

( * ) Notice: Subject to any disclaimer, the term of this patent is extended or adjusted under 35 U.S.C. 154(b) by 0 days.

(21) Appl. No.: 15/552,713

(22) PCT Filed: Feb. 25, 2016

(86) PCT No.: PCT/FI2016/050120
§ 371 (c)(1),
(2) Date: Aug. 22, 2017

(87) PCT Pub. No.: WO2016/135386
PCT Pub. Date: Sep. 1, 2016

(65) Prior Publication Data
US 2018/0264323 A1    Sep. 20, 2018

(30) Foreign Application Priority Data
Feb. 27, 2015    (FI) .................................... 20155132

(51) Int. Cl.
*A63B 26/00*    (2006.01)
*G09B 19/00*    (2006.01)
(Continued)

(52) U.S. Cl.
CPC ........ *A63B 26/003* (2013.01); *A63B 21/0004* (2013.01); *A63B 21/4035* (2015.10);
(Continued)

(58) Field of Classification Search
CPC .............. A63B 26/003; A63B 71/0622; A63B 22/0002; A63B 21/0004; A63B 24/0062;
(Continued)

(56) References Cited

U.S. PATENT DOCUMENTS 4,912,662 A * 3/1990 Butler ...................... G01C 9/06
324/663
5,846,171 A * 12/1998 Hollowell .............. A63B 21/28
482/148
(Continued)

FOREIGN PATENT DOCUMENTS

CN    103 638 642 A    3/2014
CN    103638642 A    3/2014
(Continued)

OTHER PUBLICATIONS

Supplementary European Search Report received in European Patent Application No. 16754807.2, dated Jun. 17, 2018, 1 pg.
(Continued)

*Primary Examiner* — Garrett K Atkinson
(74) *Attorney, Agent, or Firm* — Eversheds Sutherland (US) LLP

(57) ABSTRACT

The invention relates to a device (100) for performing exercises, comprising a housing (105), a deviation sensor (140) for detecting a deviation of said housing (105) from an equilibrium, and a control unit (110) coupled to said deviation sensor (140) arranged to count deviations from the equilibrium.

15 Claims, 3 Drawing Sheets

(51) Int. Cl.
| | |
|---|---|
| *A63B 21/00* | (2006.01) |
| *H04Q 9/00* | (2006.01) |
| *G09B 5/00* | (2006.01) |
| *G06F 19/00* | (2018.01) |
| *G16H 40/63* | (2018.01) |
| *A63B 22/00* | (2006.01) |
| *A63B 24/00* | (2006.01) |
| *A63B 71/06* | (2006.01) |
| *H04M 1/725* | (2006.01) |
| *G16H 20/30* | (2018.01) |

(52) U.S. Cl.
CPC ...... *A63B 21/4043* (2015.10); *A63B 22/0002* (2013.01); *A63B 24/0062* (2013.01); *A63B 24/0087* (2013.01); *A63B 71/0622* (2013.01); *G09B 5/00* (2013.01); *G09B 19/0038* (2013.01); *G16H 20/30* (2018.01); *G16H 40/63* (2018.01); *H04Q 9/00* (2013.01); *A63B 2022/0092* (2013.01); *A63B 2024/0015* (2013.01); *A63B 2024/0078* (2013.01); *A63B 2071/0625* (2013.01); *A63B 2071/0652* (2013.01); *A63B 2071/0655* (2013.01); *A63B 2220/17* (2013.01); *A63B 2220/40* (2013.01); *A63B 2220/801* (2013.01); *A63B 2220/803* (2013.01); *A63B 2220/836* (2013.01); *A63B 2225/02* (2013.01); *A63B 2225/20* (2013.01); *A63B 2225/54* (2013.01); *A63B 2230/06* (2013.01); *A63B 2230/436* (2013.01); *H04M 1/7253* (2013.01); *H04Q 2209/823* (2013.01)

(58) Field of Classification Search
CPC ............ A63B 24/0087; A63B 21/4043; A63B 21/4035; A63B 2225/20; A63B 2220/836; A63B 2024/0078; A63B 2024/0015; A63B 2220/17; A63B 2220/801; A63B 2220/803; A63B 2225/54; A63B 2225/02; A63B 2071/0655; A63B 2022/0092; A63B 2071/0625; A63B 2071/0652; A63B 2230/436; A63B 2230/06; A63B 2220/40; G16H 40/63; G09B 19/0038; G09B 5/00; G06F 19/3481; H04M 1/7253; H04Q 9/00; H04Q 2209/823
See application file for complete search history.

(56) References Cited

U.S. PATENT DOCUMENTS

| | | | | |
|---|---|---|---|---|
| 6,436,019 | B1 * | 8/2002 | Hollowell | A63B 21/28 482/148 |
| 7,292,151 | B2 * | 11/2007 | Ferguson | A61B 5/1124 340/407.1 |
| 7,492,268 | B2 * | 2/2009 | Ferguson | A61B 5/1124 340/407.1 |
| 7,722,510 | B2 * | 5/2010 | Jhu | A63B 21/0004 482/106 |
| 7,952,483 | B2 * | 5/2011 | Ferguson | A63F 13/211 340/13.2 |
| 8,159,354 | B2 * | 4/2012 | Ferguson | A63F 13/211 340/12.22 |
| 8,427,325 | B2 * | 4/2013 | Ferguson | A61B 5/1126 340/12.22 |
| 9,427,659 | B2 * | 8/2016 | Ferguson | A63F 13/211 |
| 2006/0022833 | A1 * | 2/2006 | Ferguson | A61B 5/1124 340/573.1 |
| 2006/0229159 | A1 * | 10/2006 | Nagata | A63B 22/16 482/1 |
| 2006/0293617 | A1 * | 12/2006 | Einav | A61H 1/0274 601/33 |
| 2007/0184953 | A1 * | 8/2007 | Luberski | A63B 22/18 482/146 |
| 2008/0061949 | A1 * | 3/2008 | Ferguson | A61B 5/1124 340/407.1 |
| 2009/0149257 | A1 * | 6/2009 | Ferguson | A61B 5/1124 463/37 |
| 2009/0215592 | A1 * | 8/2009 | Jhu | A63B 21/0004 482/110 |
| 2010/0173276 | A1 * | 7/2010 | Vasin | A63B 24/0006 434/307 R |
| 2011/0201428 | A1 * | 8/2011 | Ferguson | A61B 5/1124 463/37 |
| 2012/0029696 | A1 * | 2/2012 | Ota | A61H 3/04 700/250 |
| 2012/0178534 | A1 * | 7/2012 | Ferguson | A61B 5/1124 463/37 |
| 2013/0303286 | A1 * | 11/2013 | Ferguson | A61B 5/1124 463/37 |
| 2014/0005811 | A1 * | 1/2014 | Mikan | A63B 24/0062 700/91 |
| 2014/0295983 | A1 | 10/2014 | Nooner | |

FOREIGN PATENT DOCUMENTS

| | | |
|---|---|---|
| DE | 10 2010 011136 A1 | 9/2011 |
| DE | 102010011136 A1 | 9/2011 |
| JP | 2010-088724 A | 4/2010 |
| KR | 2014 0112130 A | 9/2014 |
| KR | 20140112130 A | 9/2014 |

OTHER PUBLICATIONS

Anonymous: "Bar Sensei", Feb. 14, 2015 (Feb. 14, 2015), pp. 1-5, XP055486838, Retrieved from the Internet: URL:https://web.archive.org/web/20150214082953/http:/lassess2perform.com:80/barsensei.html [retrieved on Jun. 21, 2018].

International Search Report and Written Opinion for PCT/FI2016/050120, dated May 23, 2016 (14 pages).

Search Report issued in Finnish Application No. 20155132, dated Apr. 30, 2015 (1 page).

EPO Communication dated Apr. 14, 2020.

* cited by examiner

EXERCISE DEVICE

CROSS-REFERENCE TO RELATED APPLICATIONS

This application is a U.S. National Stage application of PCT/FI2016/050120, filed 25 Feb. 2016, which claims priority to Finland Patent Application No. 20155132, filed 27 Feb. 2015. The contents of these applications are hereby incorporated by reference.

BACKGROUND

Training and workout are important for maintaining good condition and thus, wellbeing of people. Various training equipment exist to help and motivate people to move and exercise more. Training equipment is frequently used in group exercise classes that are becoming more and more popular.

It is noticed that it would be beneficial to have a training device to improve balance and coordination. Different kinds of balance boards are available in the market but they are not suitable for certain balance exercises. For example, if one wants to move, for example dance, during the balance exercise, different kind of training device is needed.

There is, therefore, a need for a new training device.

SUMMARY

Now there has been invented an improved device, by which the above problems are alleviated. Various aspects of the invention include a device, an apparatus, a computer readable medium comprising a computer program stored therein, which are characterized by what is stated in the independent claims. Various embodiments of the invention are disclosed in the dependent claims.

According to a first aspect, there is provided a device for performing exercises, comprising a housing, a deviation sensor for detecting a deviation of said housing from an equilibrium, and a control unit coupled to said deviation sensor arranged to count deviations from the equilibrium.

According to an embodiment, the device further comprises at least two handholds placed symmetrically around a center of gravity of the device.

According to an embodiment, the device further comprises means for fitting the device to at least one part of a user's body.

According to an embodiment, the device further comprises a deviation indicator for indicating the deviation from the equilibrium.

According to an embodiment, the device further comprises a timer coupled to said control unit, and means for indicating an ending of the exercise using said timer.

According to an embodiment, the device further comprises a battery level indicator.

According to an embodiment, said control unit is further arranged to calculate a trajectory of the device, and determine one or more deviation points in the trajectory, in which deviation points a deviation from equilibrium has occurred.

According to an embodiment, said control unit is further arranged to calibrate the deviation sensor for detecting the deviation of said housing from the equilibrium.

According to an embodiment, said control unit is further arranged to receive parameters, wherein said parameters comprise one or more from the group of: a threshold value for the deviation from the equilibrium, a threshold value for duration of the deviation from the equilibrium, and/or length of an exercise in time.

According to an embodiment, the device further comprises at least two handholds placed symmetrically around a center of gravity of the device, a grip detector for detecting a grip on the handholds, and wherein said control unit is configured to determine exercise settings based on said detecting, said exercise settings comprising one or more from the group of: a threshold value for the deviation from the equilibrium, a threshold value for duration of the deviation from the equilibrium and/or length of an exercise in time.

According to an embodiment, said control unit is further arranged to form a communication connection with a computer, collect exercise data during the exercise, send said exercise data to the computer through the communication connection, wherein said exercise data comprises one or more from the group of: the number of deviations from the equilibrium; the one or more deviation point in the trajectory, duration of the deviation from the equilibrium and/or time points of the deviations from the equilibrium.

According to an embodiment, the device further comprises means for receiving a trigger of an ending of the exercise through the communication connection means for indicating the ending of the exercise based on said trigger.

According to a second aspect, there is provided an apparatus comprising means for forming a communication connection with at least one training device, means for receiving user input through a user interface, means for providing exercise settings based on said user input and means for sending exercise settings to the at least one training device through the communication connection.

According to a third aspect, there is provided a computer program product embodied on a non-transitory computer readable medium, comprising computer program code configured to, when executed on at least one processor, cause an apparatus to form a communication connection with at least one training device, receive parameters from a user, form said exercise settings based on said received parameters, and send said exercise settings to the at least one training device through the communication connection.

According to a fourth aspect, there is provided a computer program embodied on a non-transitory computer readable medium, comprising computer program code configured to, when executed on at least one processor, cause an apparatus to form a communication connection with at least one training device, send a trigger of an ending of an exercise to the at least one training device through the communication connection.

DESCRIPTION OF THE DRAWINGS

In the following, various embodiments of the invention will be described in more detail with reference to the appended drawings, in which.

DESCRIPTION OF EXAMPLE EMBODIMENTS

In the following, several embodiments of the invention will be described in the context of a training device for balance training.

Figure 1:
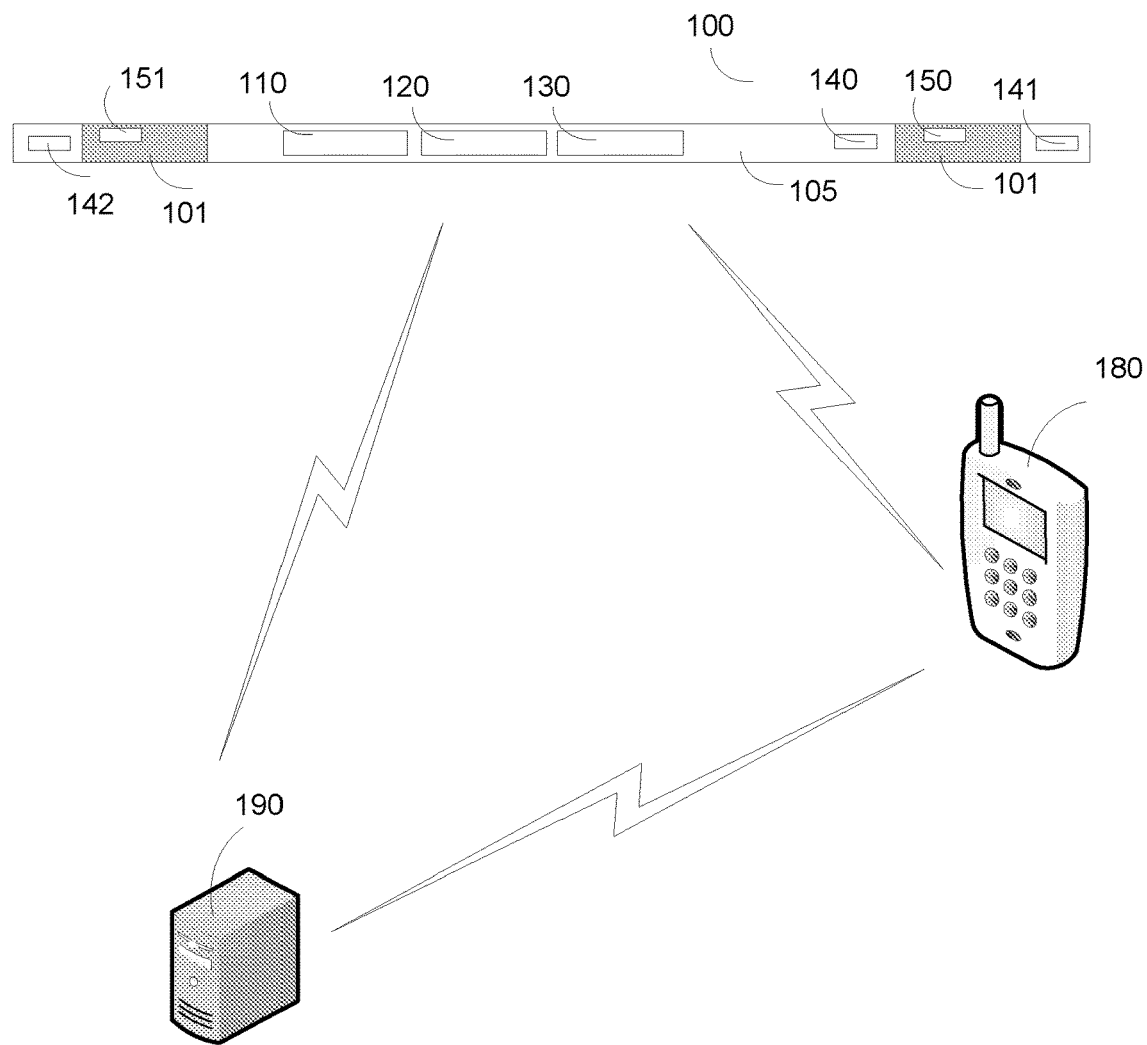
FIG. 1 shows examples of user devices.

FIG. 1 shows examples of user devices. It is shown a device for performing exercises, comprising a housing 105, a deviation sensor 140 for detecting a deviation of said housing 105 from an equilibrium and a control unit 110 coupled to said deviation sensor 140 arranged to count deviations from the equilibrium. The housing 105 of the training device 100 may be an elongated object, such as a stick. It is important to notice, that there may be various forms for the housing 105. For example, the housing 105 may be a hoop, or it may be a wristband, or an ankle band.

The training device 100 may comprise handholds 101, 102. There may be at least two handholds 101, 102 placed symmetrically around a center of gravity of the training device 100. The number of the handholds may also be larger. For example, the training device 100 may comprise four or six handholds located in a way that the grip from the handholds is symmetric around a center of gravity of the training device 100. A difficulty of the balance exercise may be adjusted by gripping the training device 100 by different handholds. For example, a grip where the hands are close to each other may lead to a difficult balance exercise while the grip where the hands are close to ends of the training device 100 may lead to easier balance exercise.

There may be other means (not shown) for fitting the training device 100 to a part of a user's body. For example, the training device 100 may comprise a strap attached to the both ends of the training device 100. The strap may be tight enough to hold the stick still when the stick is fitted on a user in a way that the user is inside a loop which is formed by the stick and the strap attached to it. For example, the stick may be fitted this way on the hips of the user, or on the back of the user. The strap may be a flexible strap.

The straps may also be attached in another way. For example, there may be two straps attached, for example, in the middle of the training device 100. The user may fit the stick on the back of the user in vertical position by tying the straps around one's torso.

The training device 100 may comprise a grip detector for detecting a grip on the handholds, and the control unit 110 may be configured to determine exercise settings based on the detecting. For example, there may be touch sensors 150, 151 integrated in the handholds 101, 102. Thus, it may be possible to detect the grip on the handholds 101, 102, and in case the training device comprises more handholds, it may be possible to find out, which handholds the user takes the grip on. This information may be sent to a computer, for example. There may be various exercise programs with different stages of difficulty, and the information on the grip may be used to choose a certain exercise program.

There may be electrodes or sensors (not shown) integrated in the handholds. These electrodes may be used to measure, for example, heart rate, oxygen saturation or other measure from the user.

The training device 100 may comprise a control unit 110. There may be a timer coupled to the control unit 110, and means, for example a vibration module 130, for indicating a beginning and/or ending of the exercise using said timer. The timer may be used to record the length of the exercise and the time points of the deviations from the equilibrium. When it is noticed that a deviation from the equilibrium occurs always at the same time point in some specific exercise, it may be possible to pay special attention to that point.

The training device 100 may comprise a display 120. The user may follow the exercise from the display. For example, the number of deviations from the equilibrium, the amount of inclination (degrees) from the equilibrium, the length of the exercise etc. may be displayed on the display 120. Alternatively or in addition, the exercise data may be transferred to another device, for example a computer or a mobile device, through a communication connection.

The training device 100 may comprise a deviation indicator, such as a vibration module 130 coupled to the control unit 110, for indicating the deviation from the equilibrium. The vibration module may evoke the training device 100 to vibrate in various situations. For example, when a deviation from the equilibrium is detected, the deviation is indicated to the user using the vibration module 130. The length of the vibration may be predetermined in user settings.

As another example, the vibration module 130 may be turned on when an exercise is about to begin and/or to end. This property may be useful in group exercise classes. A leader of the exercise may use a customized application, run by a computer or a mobile device, for group exercise and set an exercise to begin and/or end. As a consequence, the training device of each participant may vibrate to indicate that the exercise begins and/or ends. In addition to the vibration module 130, there may be other options to indicate the above mentioned events. Other possible indicators may be light, for example a LED-light, or an audio signal. In the latter case, there may be a loud speaker integrated in the training device 100.

The vibration module 130 may be turned on when battery level of the training device is getting low. Alternatively, or in addition, there may be other kind of a battery level indicator, such as a light. The vibration module 130 may be set to alert, if the training device has not been used for some time, for example for two days or for a week. Alternatively or in addition, the customized application may alert when the battery level is low and/or it would be time for an exercise.

The training device 100 may comprise various sensors 140, 141, 142 coupled to the control unit 110. For example, the sensors may comprise 9-DOF (degrees of freedom) sensors, 6-DOF sensors, motion sensors, orientation sensors, accelerometers, magnetometers or gyroscopes. These sensors, or some of these, may be used to detect a deviation from the equilibrium. The sensors are connected to the control unit 110, wherein the number of deviations from the equilibrium may be counted based on data received from the sensors.

The training device 100 may comprise a virtual sensor, for example a deviation sensor, which may be a combination of several sensors, such as an accelerometer, magnetometer and gyroscope.

The combination of an accelerometer, magnetometer and gyroscope may be used to infer the orientation of the training device 100 in 3D space. In other words, it may be possible to define pitch, roll and yaw of the training device 100. In addition, it may be possible to define linear acceleration forces in three direction (x, y, z), i.e. the gravity vector. When the attitude and the gravity vector of the training device 100 is known, it may be possible to calculate the movement of the training device 100, i.e. a trajectory. Possibility to calculate the trajectory of the training device 100 may be useful if one wants to follow in which points in the trajectory the deviations from equilibrium occur. This may be useful in physical rehabilitation, for example. When it is noticed that a deviation from the equilibrium occurs always at the same point in some specific exercise, it may be possible to pay special attention to that point.

The control unit is arranged to calibrate the deviation sensor for detecting the deviation of said housing from the equilibrium. Depending on the priorities of the user, the training device may be used in vertical or horizontal position, or some other position. The user may set in user settings, which position is the equilibrium. For example, the user may place the housing on a table or on the floor which is known to be horizontally level. Alternatively, the user may place the housing against a wall which is known to be vertically level. When the housing is on the appropriate equilibrium position, a calibration button may be pushed to calibrate the training device. Alternatively, the calibration may be carried out using an application with a computer or a mobile device.

The user may set various parameters in user settings. The training device may comprise necessities, for example buttons, for adjusting the settings, and the settings may be viewed on the display 120. Alternatively, the user may receive the user settings from another device, for example, a computer. The user settings may comprise a threshold value for the deviation from the equilibrium. This means that when the deviation exceeds the threshold, the deviation is counted and it may be indicated to the user for example using the vibration module 130. The user settings may comprise a threshold value for duration of the deviation from the equilibrium. This means that when the exceeding of the threshold value for the deviation lasts a certain time, the deviation is counted and it may indicated to the user for example using the vibration module 130. Further, the user settings may comprise length of an exercise in time. The user may decide that one wants to exercise for a half an hour, for example. When the set exercise time is full, it may be indicated to the user, for example using the vibration module 130.

The control unit 110 may be arranged to form a communication connection with other devices, such as a computer or a server 190 or a mobile device 180. Control unit 110 may be arranged to receive parameters through the communication connection, collect exercise data during the exercise and send exercise data to the computer through the communication connection. The exercise data may comprise, for example, the number of deviations from the equilibrium, the one or more deviation point in the trajectory, duration of the deviation from the equilibrium, time points of the deviations from the equilibrium, length of the exercise, heart rate of the user during the exercise etc. There may be predetermined scoring system for the exercise. Further, the user may share the exercise data in social media using a mobile device, for example. The server 190 may comprise a database for storing exercise data, and user profiles of the users of the training device. The users may see the data of each other and they may compare the exercise results and the scores with each other.

The control unit 110 may be arranged to receive commands through the communication connection. The training device may be operated using the application, for example with a mobile device. Since it is possible to operate the training device with the application, it is possible to operate various training devices at the same time. For example, in a group exercise class, all the participants may place the training device on the floor and the leader may calibrate the training devices using the application. Thus, the participants may not need to calibrate the training devices one by one. The leader may be able to see from the user interface of the application, if battery level of a training device is getting low. There may be identifiers on the training devices, for example RFID or serial numbers, which may be registered in the application. Thus, it is possible to find out which training device is running out of power.

Figure 2A:
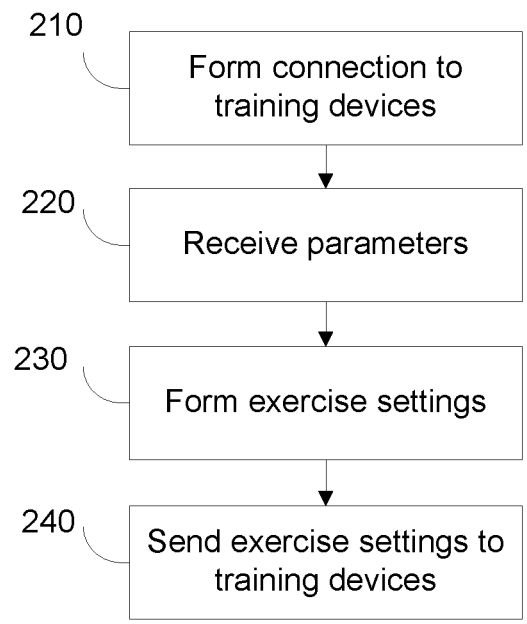
FIGS. 2a and 2b show flowcharts of examples of instructing an exercise.
Figure 2B:
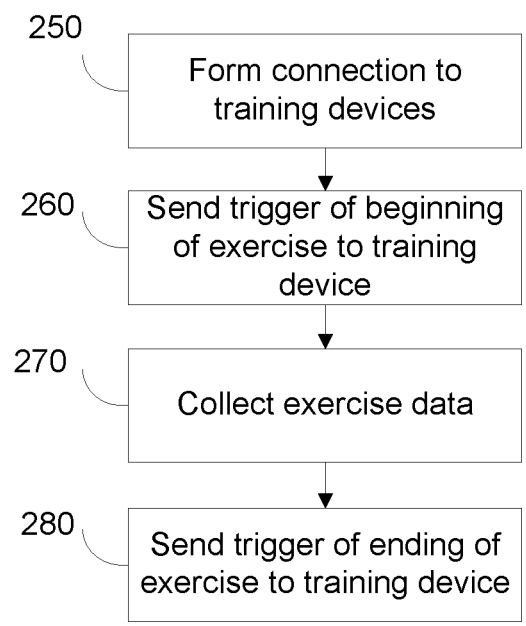

FIGS. 2a and 2b show flowcharts of examples of instructing an exercise. In a group exercise class, a leader may adjust exercise settings by using a special exercise application. The application may be a computer program product embodied on a non-transitory computer readable medium, comprising computer program code configured to, when executed on at least one processor, cause an apparatus to form 210 a communication connection with at least one training device 100, receive 220 parameters from a user, form 230 exercise settings based on received parameters, and send 240 exercise settings to the at least one training device through the communication connection.

There may be a list of different exercise settings stored in a server. The leader may choose exercise settings from the list and the exercise settings may be provided to a training device through a communication connection.

As another example, the computer program code may be configured to cause an apparatus to form 250 a communication connection to at least one training device 100, send 260, 280 a trigger of a beginning and/or an ending of the exercise to the at least one training device 100 through the communication connection. The training device 100 may collect 270 exercise data during the exercise. The training device 100 may comprise means for receiving the trigger of the ending of the exercise and means for indicating the ending of the exercise based on the trigger. For example, the trigger may cause the training device 100 to vibrate by the vibration module 130. It is important to notice that the users of different training devices may each do a different exercise based on the exercise settings.

The application may be a mobile application. Different users may load the application to their mobile devices, and they may do the exercise for example at their home. A communication connection may be formed between their training device and the mobile device. They can follow the instructed exercise on the screen of the mobile device or on another screen.

Figure 3:
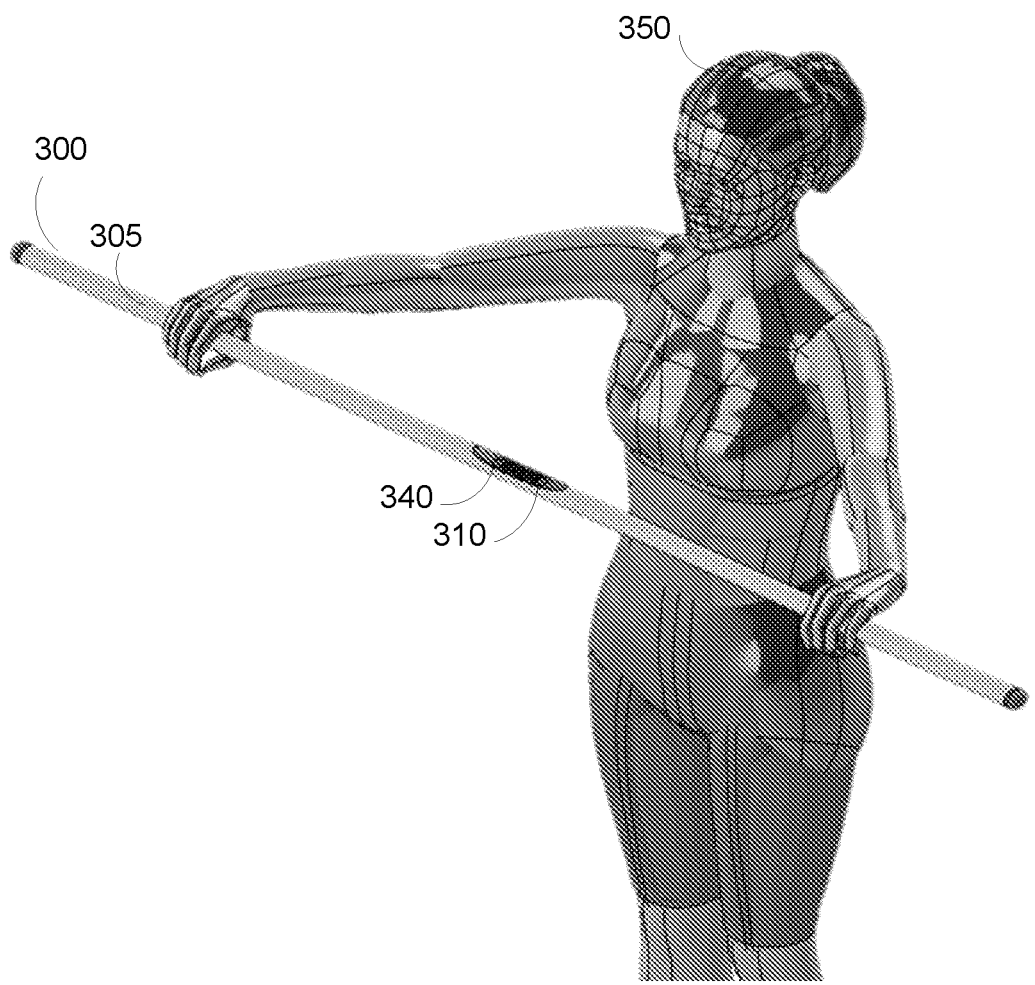
FIG. 3 shows a user holding a balance device for performing exercises.

FIG. 3 shows a user 350 holding a balance device 300 in a horizontal position, i.e. in a horizontal equilibrium. In other words, the device may be horizontally level or parallel to the floor or the ground the user is standing on. Alternatively, the user may hold the device 300 in a vertical position, i.e. in a vertical equilibrium. When the device is in the vertical position, the device may be parallel to the wall. In other words, horizontal and vertical can be understood in relation to the earth's gravitational field. Directions designated as horizontal or vertical may be observed in different ways. For example, verticality may be observed using e.g. a plumb-bob, which is a weight that is suspended from a string and may be used as a vertical reference line. Horizontality may be observed using e.g. a bubble level that exploits the buoyancy of an air bubble which naturally rests in the centre of a curved tube filled with a liquid (e.g. alcohol) and which travels away from the marked center position when the bubble level is inclined. During an exercise, the device may deviate from the horizontal equilibrium (or from the vertical equilibrium). The balance device 300 may comprise a housing 305, a deviation sensor 340 arranged to detect a deviation of said housing 305 from a horizontal or vertical equilibrium, and a control unit 310 coupled to said deviation sensor 340 arranged to count deviations from the horizontal or vertical equilibrium.

The various embodiments may provide advantages. A training device which may be held by user's hands or which may be attached to some part of the user's body enables the user to move freely during the exercise. Possibility to count the deviations from the equilibrium during the exercise gives direct feedback of the exercise. The exercise data collected by the device gives valuable information on the success of the training.

It is obvious that the present invention is not limited solely to the above-presented embodiments, but it can be modified within the scope of the appended claims.

The invention claimed is:

1. A balance device for performing exercises, comprising:
an elongated tubular housing;
at least two handholds disposed symmetrically around a center of gravity of the device;
one or more grip sensors disposed at the at least two handholds;
a deviation sensor disposed within the elongated tubular housing arranged to detect a deviation of the housing from a horizontal or vertical equilibrium; and
a control unit coupled to the deviation sensor configured to:
  count a number of deviations from the horizontal or vertical equilibrium.

2. The device according to claim 1, further comprising:
means for fitting the device to at least one part of a user's body.

3. The device according to claim 1, further comprising:
a deviation indicator for indicating the deviation from the equilibrium.

4. The device according to claim 1, further comprising:
a timer coupled to the control unit; and
means for indicating an ending of the exercise using the timer.

5. The device according to claim 1, further comprising:
a battery level indicator.

6. The device according to claim 1, wherein the control unit is further configured to:
calculate a trajectory of the device; and
determine one or more deviation points in the trajectory, in which deviation points a deviation from equilibrium has occurred.

7. The device according to claim 1, wherein the control unit is further a configured to:
calibrate the deviation sensor for detecting the deviation of the housing from the equilibrium.

8. The device according to claim 1, wherein the control unit is further configured to:
receive parameters, wherein the parameters comprise at least one of:
  a threshold value for the deviation from the equilibrium;
  a threshold value for duration of the deviation from the equilibrium; and
  length of an exercise in time.

9. The device according to claim 1,
wherein the control unit is configured to determine exercise settings based on the detecting, the exercise settings comprising at least one of:
  a threshold value for the deviation from the equilibrium;
  a threshold value for duration of the deviation from the equilibrium; and
  length of an exercise in time.

10. The device according to claim 1, wherein the control unit is further configured to:
form a communication connection with a computer;
collect exercise data during the exercise; and
send the exercise data to the computer through the communication connection wherein the exercise data comprises at least of:
  the number of deviations from the horizontal or vertical equilibrium;
  the one or more deviation point in the trajectory;
  a duration of the deviation from the horizontal or vertical equilibrium; and
  time points of the deviations from the horizontal or vertical equilibrium.

11. The device according to claim 10, wherein the control unit is further configured to:
receive a trigger of an ending of the exercise through the communication connection; and
indicate the ending of the exercise based on the trigger.

12. An apparatus comprising a processor configured to:
establish a communication connection with a training device comprising:
  an elongated tubular housing;
  at least two handholds disposed symmetrically around a center of gravity of the device;
  one or more grip sensors disposed at the at least two handholds; and
  a deviation sensor disposed within the elongated tubular housing arranged to detect a deviation of the housing from a horizontal or vertical equilibrium;
receive a user input through a user interface;
provide an exercise setting based on the user input; and
send the exercise setting to the training device through the communication connection.

13. A computer program product embodied on a non-transitory computer readable medium, comprising computer program code configured to, when executed on at least one processor, cause an apparatus to:
form a communication connection with a training device comprising:
  an elongated tubular housing;
  at least two handholds disposed symmetrically around a center of gravity of the device;
  one or more grip sensors disposed at the at least two handholds; and
  a deviation sensor disposed within the elongated tubular housing arranged to detect a deviation of the housing from a horizontal or vertical equilibrium;
receive parameters from a user;
form the exercise settings based on the received parameters; and
send the exercise settings to the training device through the communication connection.

14. A computer program product embodied on a non-transitory computer readable medium, comprising computer program code configured to, when executed on at least one processor, cause an apparatus to:
form a communication connection with at least one training device according to claim 1; and
send a trigger of an ending of an exercise to the at least one training device through the communication connection.

15. The device according to claim 1, wherein the control unit is further configured to provide an instruction to a user to switch a grip from a first set of corresponding handholds to a second set of corresponding handholds, the first set of corresponding handholds and the second set of corresponding handholds being located at different locations on the device.

* * * * *